United States Patent
Sanai

(10) Patent No.: US 9,566,106 B2
(45) Date of Patent: Feb. 14, 2017

(54) SURGICAL DEVICE

(71) Applicant: OLYMPUS CORPORATION, Tokyo (JP)

(72) Inventor: Hideo Sanai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/163,528

(22) Filed: Jan. 24, 2014

(65) Prior Publication Data

US 2014/0194871 A1 Jul. 10, 2014

Related U.S. Application Data

(63) Continuation of application No. PCT/JP2013/060447, filed on Apr. 5, 2013.
(Continued)

(51) Int. Cl.
*A61B 18/14* (2006.01)
*A61B 17/32* (2006.01)
(Continued)

(52) U.S. Cl.
CPC ....... *A61B 18/14* (2013.01); *A61B 17/320092* (2013.01); *A61B 18/1445* (2013.01);
(Continued)

(58) Field of Classification Search
CPC ............ A61B 17/320092; A61B 18/14; A61B 18/1445; A61B 2218/002; A61B 2218/007; A61B 18/12; A61B 2017/00026; A61B 2018/00029; A61B 2018/00684; A61B 2018/00744; A61B 2018/00761; A61B 2018/00875; A61B 2018/00994; A61B 2217/007; A61B 2218/00
See application file for complete search history.

(56) References Cited

U.S. PATENT DOCUMENTS 5,279,547 A 1/1994 Costin
5,417,709 A * 5/1995 Slater ........................... 606/205
(Continued)

FOREIGN PATENT DOCUMENTS

CN 102138823 A 8/2011
JP A-2001-501513 2/2001
(Continued)

OTHER PUBLICATIONS

International Search Report issued in International Application No. PCT/JP2013/060447 dated May 7, 2013 (with translation).
(Continued)

*Primary Examiner* — Jaymi Della
(74) *Attorney, Agent, or Firm* — Oliff PLC

(57) ABSTRACT

A surgical apparatus includes: a treatment section treating a living tissue; an energy generation section providing high-frequency current to the treatment section; a liquid feeding conduit feeding a liquid to the living tissue; a suction conduit suctioning the liquid; an energy control section that outputs a high-frequency output control signal for controlling the energy generation section; a first pump drive section that feeds the liquid from the liquid feeding conduit while the high-frequency current is output, according to a command of the high-frequency output control signal, and stops feeding of the liquid, according to a command of the high-frequency output control signal; and a second pump drive section that suctions the liquid from the suction conduit for a predetermined period of time or in a predetermined amount, accord-
(Continued)

ing to a command for stopping the high-frequency output control signal, and stops suction of the liquid after the suction.

5 Claims, 10 Drawing Sheets

Related U.S. Application Data

(60) Provisional application No. 61/636,269, filed on Apr. 20, 2012.

(51) Int. Cl.
*A61B 17/00* (2006.01)
*A61B 18/00* (2006.01)

(52) U.S. Cl.
CPC ........... *A61B 2017/00026* (2013.01); *A61B 2018/00875* (2013.01); *A61B 2218/002* (2013.01); *A61B 2218/007* (2013.01)

(56) References Cited

U.S. PATENT DOCUMENTS

| | | | |
|---|---|---|---|
| 5,797,901 A | 8/1998 | Cosmescu | |
| 5,836,909 A | 11/1998 | Cosmescu | |
| 6,666,860 B1 | 12/2003 | Takahashi | |
| 8,920,415 B2 | 12/2014 | Govari | |
| 2003/0040672 A1 | 2/2003 | Ogura et al. | |
| 2004/0215181 A1* | 10/2004 | Christopherson | A61B 18/1477 606/32 |
| 2006/0015097 A1* | 1/2006 | Mulier et al. | 606/41 |
| 2006/0258975 A1 | 11/2006 | Takahashi | |
| 2006/0259029 A1* | 11/2006 | Utley et al. | 606/41 |
| 2006/0265035 A1* | 11/2006 | Yachi et al. | 607/101 |
| 2008/0167645 A1 | 7/2008 | Woloszko | |
| 2010/0042101 A1* | 2/2010 | Inagaki | A61B 18/1442 606/52 |
| 2010/0137751 A1* | 6/2010 | Tadami | 601/2 |
| 2010/0324458 A1 | 12/2010 | Okada et al. | |
| 2011/0040299 A1* | 2/2011 | Kim et al. | 606/33 |

FOREIGN PATENT DOCUMENTS

| | | |
|---|---|---|
| JP | A-2001-112768 | 4/2001 |
| JP | A-2006-187668 | 7/2006 |
| JP | A-2006-341066 | 12/2006 |
| WO | WO 98/14131 A1 | 4/1998 |

OTHER PUBLICATIONS

Dec. 23, 2015 Office Action issued in Chinese Patent Application No. 201380010521.9.
Sep. 14, 2015 Extended European Search Report issued in European Patent Application No. 13779010.1.

* cited by examiner

SURGICAL DEVICE

CROSS REFERENCE TO RELATED APPLICATION

This application is a continuation application of PCT/JP2013/060447 filed on Apr. 5, 2013 and claims benefit of U.S. Provisional Patent Application No. 61/636,269 filed in the U.S.A. on Apr. 20, 2012, the entire contents of which are incorporated herein by this reference.

BACKGROUND OF THE INVENTION

1. Field of the Invention

The present invention relates to a surgical apparatus, and specifically relates to a surgical apparatus that can output high-frequency current.

2. Description of the Related Art

Surgical treatment instruments are used for treatments such as coagulation or dissection of a living tissue in surgical operations. Among the surgical treatment instruments, there are those of a type that pinches or comes into contact with a living tissue to perform treatment (what is called a "scissors shape" or a "scoop shape" type). Also, as surgical treatment instruments, for example, high-frequency treatment instruments that can output high-frequency current have been known. As surgical treatment instruments, for example, ultrasound treatment instruments that can output ultrasound vibration, and high-frequency treatment instruments that can output high-frequency current, and furthermore, in recent years, energy treatment instruments that can simultaneously output ultrasound vibration and high-frequency current have been known.

In a scissors shape-type ultrasound treatment instrument, one of the members performs ultrasound vibration, and the other jaw member is opened/closed relative to the one member for pinching. Also, a scissors shape-type high-frequency treatment instrument provides a bipolar output of high-frequency current using two members.

There are cases where such treatment instrument is used to provide treatment using a high-frequency output while dripping saline. For example, in order to stop oozing bleeding in the parenchyma of a liver, that is, in order to stop the flow of blood oozing over a board area, a high-frequency output is provided while saline is dripped. Providing a high-frequency output with the oozing bleeding area immersed in saline enables a treatment to stop the oozing bleeding to be provided over the broad area. When such treatment to stop oozing bleeding is provided, a puddle of saline is formed inside the body, and thus, an assistant suctions the accumulated saline using a suction tube.

Also, the specifications of US Patent Application Laid-Open Publication Nos. US2010/137751A1, US2003/0040672A1 and US2010/0324458A1 each disclose a surgical apparatus that supplies a liquid to a treatment instrument and suctions the liquid during treatment.

SUMMARY OF THE INVENTION

A surgical apparatus according to an aspect of the present invention includes: a treatment section for treating a living tissue; an energy generation section for providing high-frequency current to the treatment section; a liquid feeding conduit for feeding a liquid to the living tissue; a suction conduit for suctioning the liquid; an energy control section that outputs a high-frequency output control signal for controlling the high-frequency current from the energy generation section; a first pump drive section that feeds the liquid from the liquid feeding conduit while the high-frequency current is output, in response to a command for an output of the high-frequency output control signal from the energy control section, and stops feeding of the liquid from the liquid feeding conduit, in response to a command for stopping the high-frequency output control signal; and a second pump drive section that suctions the liquid from the suction conduit for a predetermined period of time or in a predetermined amount, in response to a command for stopping the high-frequency output control signal from the energy control section, and stops suction of the liquid from the suction conduit after the suction for the predetermined period of time or in the predetermined amount.

DETAILED DESCRIPTION OF THE PREFERRED EMBODIMENTS

The present invention will be described below by means of embodiments.

First Embodiment

Figure 1:
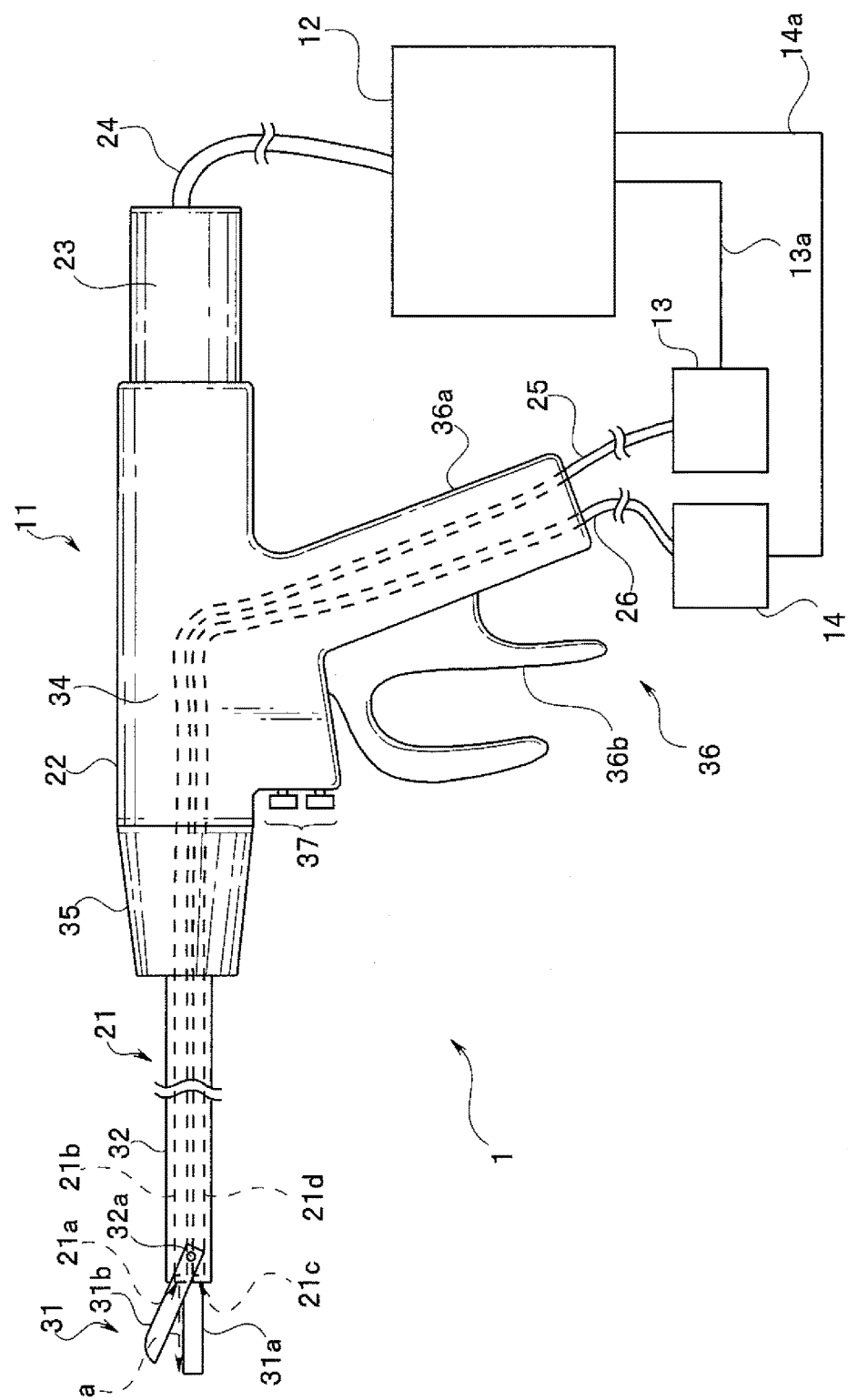
FIG. 1 is a diagram for describing a configuration of a surgical apparatus according to a first embodiment of the present invention.

FIG. 1 is a diagram for describing a configuration of a surgical apparatus according to a first embodiment of the present invention. As illustrated in FIG. 1, a surgical apparatus 1 includes a treatment instrument 11, a power supply unit 12, a liquid feeding unit 13 and a suction unit 14.

The treatment instrument 11 is a scissors shape-type surgical treatment instrument that can output at least either ultrasound vibration energy or high-frequency current energy. The treatment instrument 11 includes a treatment unit 21, a handle unit 22, a transducer unit 23, a signal cable 24 and a liquid feeding tube 25.

The treatment unit 21 includes a treatment section 31 for treating a living tissue, and an elongated sheath portion 32. The treatment section 31 includes a probe 31a, and a movable member 31b, which is a jaw member. The sheath portion 32 is a cylindrical member, and a shaft member or the like for opening/closing the probe 31a and the movable member 31b relative to each other is inserted inside the sheath portion 32. The movable member 31b can pivot with a pin 32a as a pivot axis, the pin 32a being provided at a distal end of the sheath portion 32, according to a motion of the shaft member or the like by an operation of the handle unit 22. Accordingly, a distal end portion of the probe 31a and the movable member 31b form a pinching portion that pinches a living tissue.

Furthermore, at a distal end portion of the treatment unit 21, an opening portion 21a for feeding saline is provided, and the opening portion 21a is connected to a tube 21b inserted inside the sheath portion 32. As indicated by dotted arrow a in FIG. 1, the opening portion 21a and a tube 21b are disposed so that saline is fed and dripped toward a pinching part between the probe 31a and the movable member 31b in the treatment section 31. Accordingly, the opening portion 21a is a liquid feeding port provided in the treatment section 31, for feeding saline from the tube 21b, which is a liquid feeding conduit, between a living tissue and the treatment section 31.

A proximal end portion of the tube 21b inserted also inside the handle unit 22 is connected to the liquid feeding tube 25, whereby the tube 21b and the liquid feeding tube 25 are in communication with each other. As described later, the treatment instrument 11 is configured so that saline, which is a liquid fed from the liquid feeding unit 13, can pass through the liquid feeding tube 25 and the tube 21b and be ejected from the opening portion 21a. Accordingly, the liquid feeding tube 25 and the tube 21b form a liquid feeding conduit for feeding saline.

Also, at the distal end portion of the treatment unit 21, an opening portion 21c for suctioning saline is provided, and the opening portion 21c is connected to a tube 21d inserted inside the sheath portion 32. A proximal end portion of the tube 21d inserted also inside the handle unit 22 is connected to a suction tube 26, whereby the tube 21d and the suction tube 26 are in communication with each other. As described later, the treatment instrument 11 is configured so that saline can be suctioned from the opening portion 21c via the suction tube 26 and the tube 21d by the suction unit 14. Accordingly, the suction tube 26 and the tube 21d form a suction conduit for suctioning saline.

The opening portion 21a is a liquid feeding port provided in the treatment section 31, for feeding saline from the tube 21b, which is included in the liquid feeding conduit. The opening portion 21c is a suction port provided in the treatment section 31, for suctioning saline into the tube 21d, which is included in the suction conduit.

The handle unit 22 includes a rotating knob 35 on a distal end side of a cylindrical body portion 34. A surgeon can change an orientation of the probe 31a in the treatment section 31 by rotating the rotating knob 35 around an axis of the body portion 34.

A transducer unit 23 is attached to a proximal end portion of the body portion 34. The transducer unit 23 is connected to the probe 31a. The transducer unit 23 includes an ultrasound transducer (not illustrated) inside, which enables the probe 31a to perform ultrasound vibration.

The body portion 34 includes a handle portion 36, and the handle portion 36 includes a fixed handle 36a and a movable handle 36b. The handle portion 36 is an operating handle for pinching a living tissue. When a surgeon operates the movable handle 36b so as to come close to the fixed handle 36a, that is, close the handle portion 36, the movable member 31b in the treatment section 31 pivots, enabling a living tissue to be pinched between the probe 31a and the movable member 31b.

Furthermore, in the body portion 34, a plurality of switches 37 for output operation are provided. Accordingly, the surgeon turns on relevant one(s) of the switches 37 while grasping the handle portion 36 with a living tissue pinched between the distal end portion of the probe 31a and the movable member 31b in the treatment section 31, whereby treatment using an ultrasound vibration output, a high-frequency current output or a simultaneous output of ultrasound vibration and high-frequency current can be provided.

The power supply unit 12 is a control apparatus, and as described later, includes a control section, and performs control of ultrasound vibration output and high-frequency current output, and liquid feeding and suction according to operations of the switches 37 by the surgeon.

The liquid feeding unit 13 is connected to the power supply unit 12 via a signal cable 13a. Also, the liquid feeding unit 13 is connected to the treatment instrument 11 via the liquid feeding tube 25 for liquid feeding, enabling saline to be fed from the liquid feeding unit 13 to the treatment instrument 11.

The suction unit 14 is connected to the power supply unit 12 via a signal cable 14a. Also, the suction unit 14 is connected to the treatment instrument 11 via the suction tube 26 for suction, enabling saline to be suctioned from the opening portion 21c by the suction unit 14.

Figure 2:
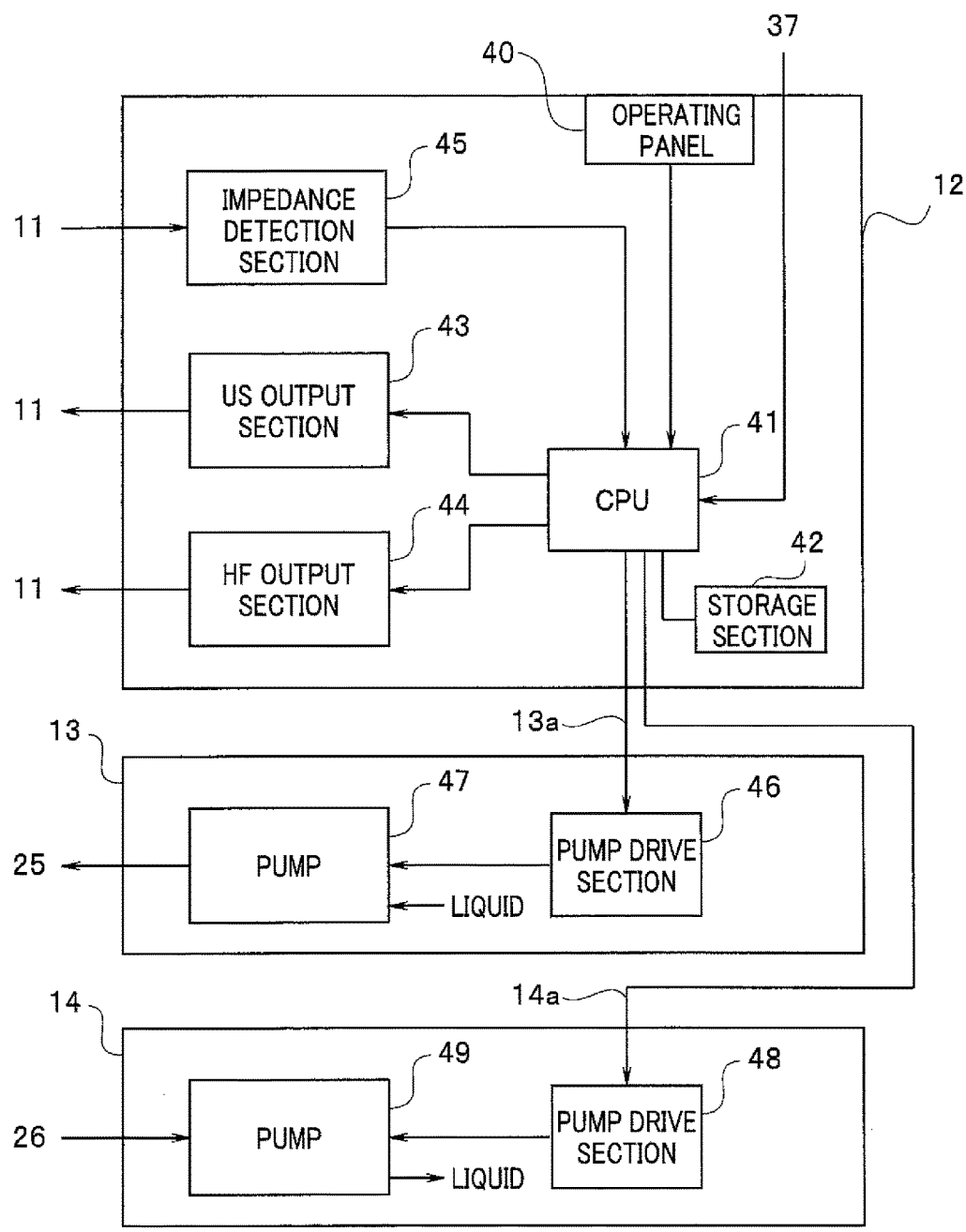
FIG. 2 is a block diagram illustrating configurations of a power supply unit 12, a liquid feeding unit 13 and a suction unit 14 according to the first embodiment of the present invention.

FIG. 2 is a block diagram illustrating configurations of the power supply unit 12, the liquid feeding unit 13 and the suction unit 14. The power supply unit 12 is a control apparatus that controls energy output of the treatment instrument 11. The power supply unit 12 includes an operating panel 40, which serves as an operating/setting section, a central processing unit (hereinafter referred to as "CPU") 41, which serves as a control section, a storage section 42, an ultrasound output section (hereinafter referred to as "US output section") 43 that outputs a drive signal for driving the transducer unit 23 for ultrasound vibration output, a high-frequency output section (hereinafter referred to as an "HF output section") 44 that outputs a high-frequency current signal for high-frequency current output, and an impedance detection section 45.

As described above, the CPU 41 controls an ultrasound vibration output, a high-frequency current output or a simultaneous output of ultrasound vibration and high-frequency current. The control is performed by the CPU 41 executing a control program stored in the storage section 42.

The storage section 42 includes, e.g., a ROM that stores the control program, a RAM that serves as a working memory area at the time of execution of the program, and a nonvolatile rewritable memory that stores information on liquid feeding time periods, which will be described later.

The US output section 43 outputs a drive signal for making the probe 31*a* perform ultrasound vibration, to the treatment instrument 11 via the signal cable 24 based on an ultrasound output control signal from the CPU 41.

The HF output section 44 outputs a high-frequency current signal for supplying a bipolar high-frequency output to the treatment section 31, to the treatment instrument 11 via the signal cable 24 based on a high-frequency output control signal from the CPU 41.

Accordingly, the US output section 43 and the HF output section 44 are energy generation sections that generate energy for providing ultrasound vibration and high-frequency current to the treatment section 31, respectively.

The impedance detection section 45 is a circuit for detecting an impedance of a living tissue pinched between the probe 31*a* and the movable member 31*b*. In other words, the impedance detection section 45 detects an impedance between two pinching members that pinch a living tissue in the treatment section 31. The impedance detection section 45 supplies a detection signal according to the impedance between the probe 31*a* and the movable member 31*b*, to the CPU 41.

Operating signals from the switches 37 are also inputted to the CPU 41. Note that here, as described later, an instruction for an energy output is provided by operation of a relevant one of the switches 37 by the surgeon; however, such energy output instruction may be provided via, e.g., a foot switch.

The liquid feeding unit 13 includes a pump drive section 46 and a pump 47. The pump drive section 46 is a drive circuit that outputs a drive signal for driving the pump 47, based on a pump drive signal from the CPU 41 via the signal cable 13*a*. The pump 47, which serves as a first pump, is connected to a non-illustrated tank, and is driven based on a drive signal from the pump drive section 46 and supplies saline retained in the tank to the tube 25. Performance of discharge by the pump 47 is, for example, 20 ml/min. In other words, the pump 47 is a pump for supplying saline to the liquid feeding conduit in order to feed a liquid of saline from the opening portion 21*a*, which is a liquid feeding port.

The suction unit 14 includes a pump drive section 48 and a pump 49. The pump drive section 48 is a drive circuit that outputs a drive signal for driving the pump 49 based on a pump drive signal from the CPU 41 via the signal cable 14*a*. The pump 49, which serves as a second pump, is connected to a non-illustrated tank, is driven based on a drive signal from the pump drive section 48, and discharges saline suctioned via the tube 26 to the tank (not illustrated). Performance of suction by the pump 49 is, for example, 20 ml/min. In other words, the pump 49 is a pump for suctioning a liquid of saline from the opening portion 21*c*, which is a suction port, via the suction conduit.

The CPU 41 controls the US output section 43 and the HF output section 44 and also controls the pump drive sections 46 and 48, according to operating signals from the switches 37.

In the storage section 42, later-described data on suction time periods for suction of saline by the pump 49, which are set in advance, is stored.

Figure 3:
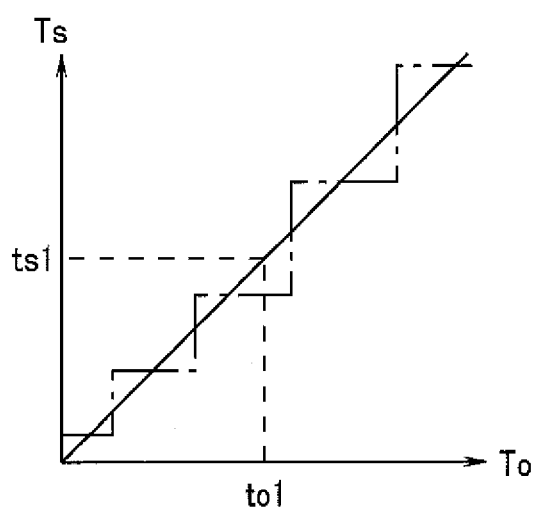
FIG. 3 is a diagram indicating a relationship between a high-frequency output time period To and a suction time period Ts, which is stored in a storage section 42, according to the first embodiment of the present invention.

FIG. 3 is a diagram indicating a relationship between high-frequency output time period To and suction time period Ts, which is stored in the storage section 42. Since high-frequency output and driving of the liquid feeding pump 47 are linked to each other, the suction time period Ts is proportional to the high-frequency output time period To. Accordingly, the suction time period Ts relative to the high-frequency output time period To is set in advance so that as the high-frequency output time period To increases, the suction time period Ts is longer, and stored in the storage section 42. The suction time period Ts according to the high-frequency output time period To is stored in the form of, for example, table data in the storage section 42. As described later, the high-frequency output time period To is equal to a period of time of driving the pump 47.

Note that the suction time period Ts according to the high-frequency output time period To can be set/changed by, e.g., a surgeon via the operating panel 40 in the power supply unit 12 according to a difference in performance between the pumps 47 and 49 and a demand from the surgeon.

In other words, for the suction time period Ts, a period of time necessary for removing saline fed for energy-used treatment by means of suction of the saline is set.

Note that in FIG. 3, the suction time period Ts is set so as to increase in linear proportion to the high-frequency output time period To; however, as indicated by the alternate long and short dash line, the suction time period Ts may be set so as to increase in a stepwise manner.

Figure 4:
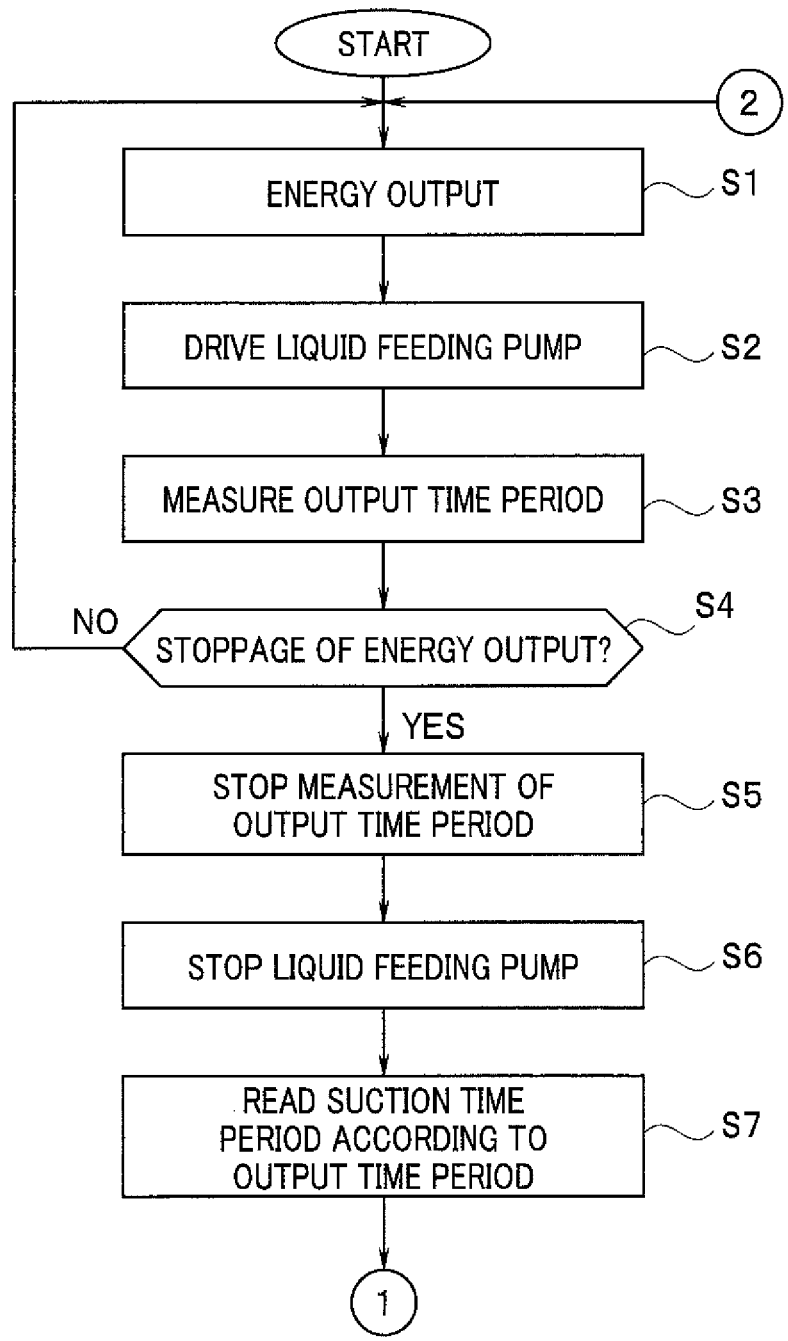
FIG. 4 is a flowchart illustrating an example of processing performed by a CPU 41 that controls an HF output section 44 and pump drive sections 46 and 48, according to the first embodiment of the present invention.
Figure 5:
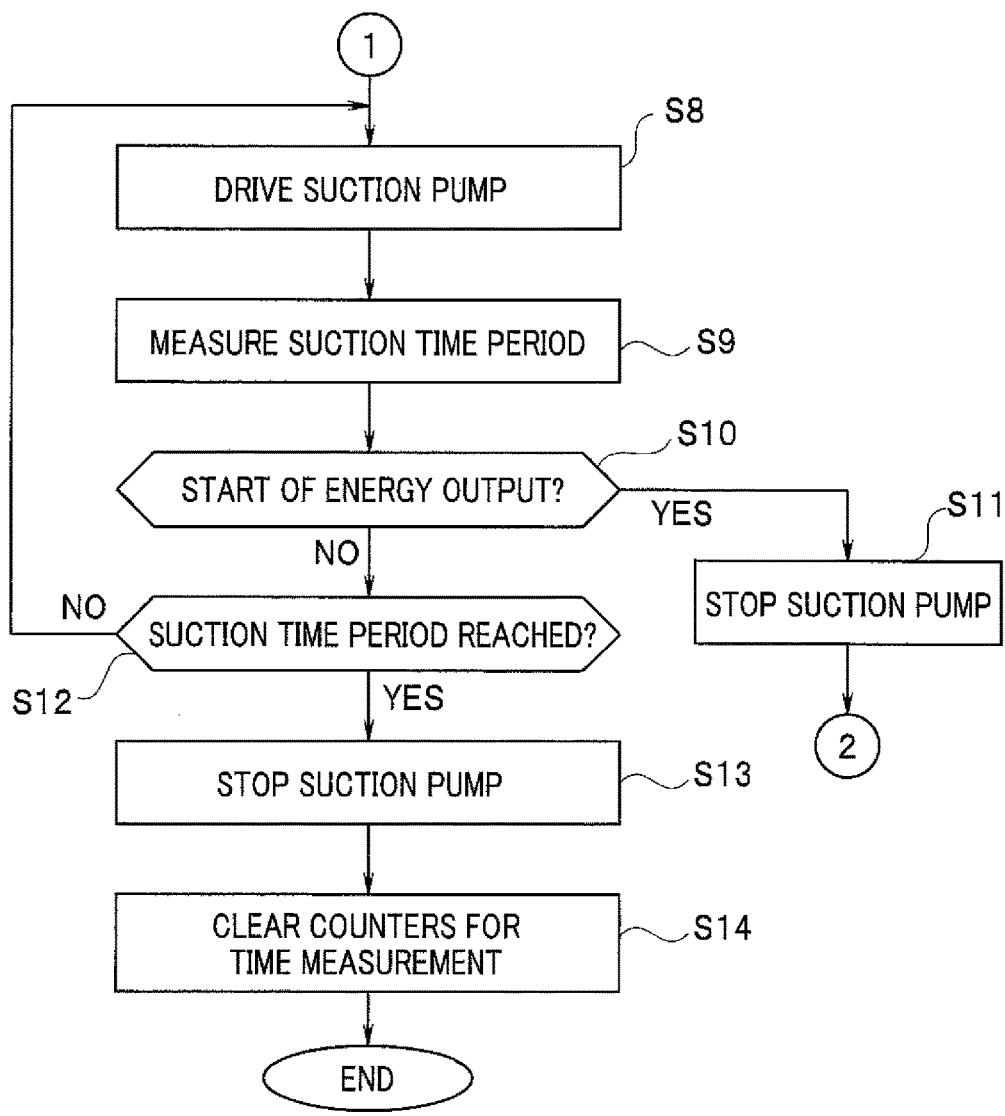
FIG. 5 is a flowchart illustrating an example of processing performed by the CPU 41 that controls the HF output section 44 and the pump drive sections 46 and 48, according to the first embodiment of the present invention.
Figure 6:
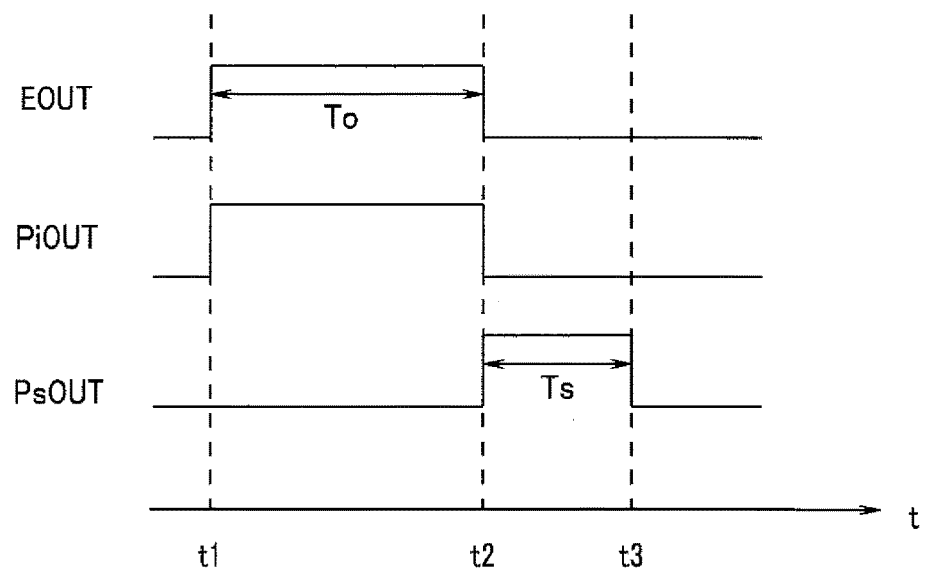
FIG. 6 is a timing chart of an output signal EOUT for a high-frequency current output and pump drive signals PiOUT and PsOUT for pumps 47 and 49 according to the first embodiment of the present invention.

FIGS. 4 and 5 are flowcharts illustrating an example of processing performed by the CPU 41 that controls the HF output section 44 and the pump drive sections 46 and 48. FIG. 6 is a timing chart of an output signal EOUT for a high-frequency current output and pump drive signals PiOUT and PsOUT for the pumps 47 and 49.

The processing in FIG. 4 is processing performed by the CPU 41 when a relevant one of the switches 37 is depressed and hereby turned on to provide an instruction for an energy output of high-frequency current.

Upon receipt of an instruction for an energy output provided by depression of a relevant one of the switches 37, the CPU 41 provides an energy output designated by the instruction (S1). If the energy output is a high-frequency current output, the HF output section 44 is driven so as to provide a predetermined or designated output. Simultaneously with the energy output, the CPU 41 outputs a pump drive signal PiOUT to the pump drive section 46 to drive the liquid feeding pump 47 (S2). In FIG. 6, an output signal EOUT becomes high at a time t1, whereby energy output and liquid feeding are started.

The CPU 41 starts time measurement using, e.g., a software counter, simultaneously with the energy output, to measure a period of time of the output of the high-frequency current (S3).

Then, the CPU 41 determines whether or not the switch 37 is turned off, that is, the energy output is stopped (S4), and if the energy output is not stopped (S4: NO), the processing returns to S1. If the energy output is stopped (S4: YES), the CPU 41 stops the measurement of the output time period (S5), and stops the output of the pump drive signal PiOUT to stop the liquid feeding pump 47 (S6).

Then, the CPU 41 calculates a period of time of the energy output from a count value of the counter for output time period measurement, and reads a suction time period Ts stored in the storage section 42 based on the calculated output time period To (S7). For example, in FIG. 3, if the output time period To is to1, a value ts1 of the suction time period Ts is read.

The CPU 41 outputs a pump drive signal PsOUT to the pump drive section 48 to drive the pump 49, whereby suction is performed (S8). As a result, saline that has been fed to stop oozing bleeding and accumulated is suctioned from the opening portion 21*c* at the distal end portion of the sheath portion 32 of the treatment instrument 11. In FIG. 6, at a time t2, the energy output and the driving of the liquid feeding pump 47 are stopped and suction is started.

Note that driving of the suction pump 49 may be performed after a lapse of a predetermined period of time from stoppage of the energy output. For example, the pump 49 may be driven after a lapse of a period of time from stoppage of an energy output to the extent that a surgeon does not feel stressed about the period of time. The period of time to the extent that a surgeon does not feel stressed about the period of time is, for example, a time lag of 0.5 seconds.

Simultaneously with the start of the suction, the CPU 41 further starts time measurement using, e.g., a software counter that is separate from the counter for output time period measurement, to measure a suction time period Ts (S9).

The CPU 41 determines whether or not an instruction for a start of an energy output is provided by a relevant one of the switches 37 being operated during the suction (S10). If an energy output is started (S10: YES), the CPU 41 discontinues the output of the pump drive signal PsOUT to the pump drive section 48 to stop the pump 49, whereby the suction is stopped (S11), and the processing returns to S1. In other words, upon receipt of an instruction for generating energy to the HF output section 44, which is an energy generation section, after stoppage of an energy output, the CPU 41 stops the pump 49 to prioritize the instruction provided via a surgeon's operation.

If no energy output is started (S10: NO), whether or not a period of time passed from the start of the suction has reached the read suction time period Ts is determined (S12). The CPU 41 determines whether or not a period of time from the start of the suction has reached the read suction time period Ts. If the period of time from the start of the suction has not yet reached the suction time period Ts read from the storage section 42 (S12: NO), the processing returns to S8 and the suction is continued.

If the period of time passed from the start of the suction has reached the suction time period Ts (S12: YES), the CPU 41 stops the output of the pump drive signal PsOUT to the pump drive section 48 to stop the suction (S13), and clears the two counters used for measuring the output time period and the suction time period (S14). In FIG. 6, at a time t3, the suction is stopped.

In other words, the CPU 41, which is a control section, controls the pump 49 so that in connection with stoppage of an output of energy from the HF output section 44, which is an energy generation section, saline is suctioned by the pump 49 for a predetermined period of time after the stoppage of the energy output. More specifically, the CPU 41 performs control so that driving of the pump 49 is started in response to stoppage of an output of energy, so as to perform suction of saline by the pump 49 for a suction time period according to an energy output time period or a liquid feeding time period, and the pump 49 is stopped after suction of saline by the pump 49 for the predetermined period of time.

As a result, suction is performed during a set suction time period Ts, and thus, saline accumulated as a result of being fed at the time of energy-used treatment is suctioned in the amount of the accumulation. In other words, a surgeon performs suction of saline accumulated inside a body as a result of a treatment to stop oozing bleeding with no assistant, and thus, the accumulated saline is removed without the need for an assistant and without hindrance of the vision by a suction tube operated by an assistant, enabling the surgeon to promptly continue the surgical operation.

As described above, with the above-described surgical apparatus 1 according to the present embodiment, when, e.g., treatment for oozing bleeding is provided, saline accumulated inside the body is promptly removed, enabling a surgeon to promptly continue the surgical operation. As a result, the duration of the surgical operation can be reduced.

Second Embodiment

Although in the above-described first embodiment, in connection with stoppage of an energy output, the CPU 41 drives the pump 49 to start suction, in a second embodiment, suction is restricted by mechanically pressing the suction tube 26 or the suction tube 21d according to a pinching operation performed via the handle portion 36 and suction is started when the pinching operation is cancelled.

Figure 7:
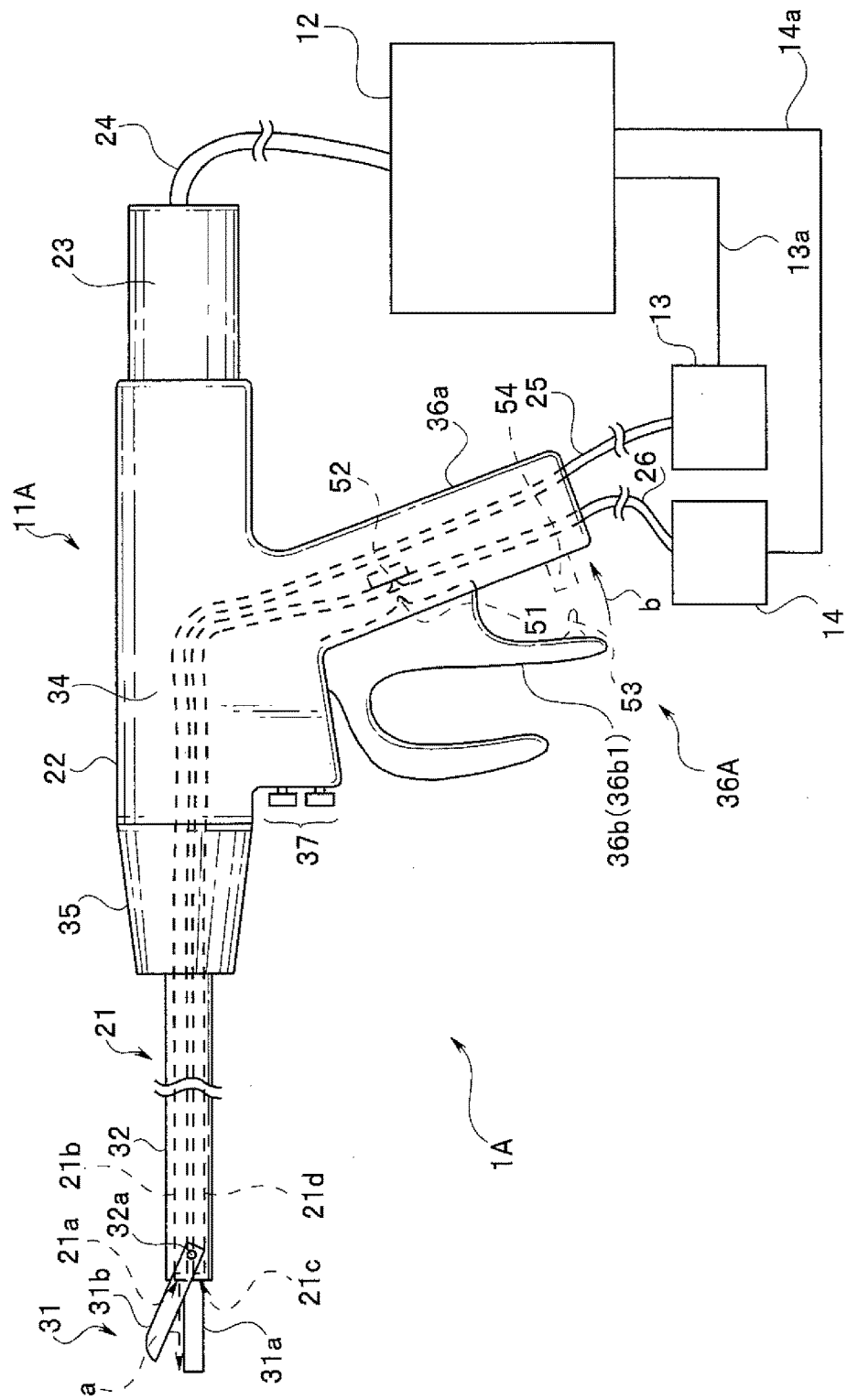
FIG. 7 is a diagram for describing a configuration of a surgical apparatus 1A according to a second embodiment of the present invention.

FIG. 7 is a diagram for describing a configuration of a surgical apparatus 1A according to the present embodiment. In FIG. 7, components that are the same as those in FIG. 1 are provided with reference numerals that are the same as those in FIG. 1, and a description thereof will be omitted. Here, a handle portion 36A is operated so as to be closed when an instruction for an energy output is provided.

In the surgical apparatus 1A, a movable handle 36b1 in a treatment instrument 11A includes a projection portion 51 that abuts against and thereby deforms a suction tube 21d when the handle portion 36A is closed. Also, inside a fixed handle 36a, a receiving member 52 that receives the suction tube 21d deformed by the projection portion 51 is provided in a fixed manner.

In other words, if the handle portion 36A is closed and the movable handle 36b1 is thereby moved in the direction indicated by solid arrow b in FIG. 7, the projection portion 51 mechanically presses the suction tube 21d against the receiving member 52 inside the fixed handle 36a to deform the suction tube 21d so that suction from the pump 49 via the suction tube 21d is stopped. If a surgeon opens the handle portion 36A, the suction tube 21d is released from the force from the projection portion 51 and thus, saline flows inside the suction tube 21d.

Accordingly, the projection portion 51 and the receiving member 52 in the handle portion 36A form a liquid suction restricting mechanism arranged at a position midway in the suction tube 21d, the liquid suction restricting mechanism restricting the flow of a suctioned liquid inside the suction tube 21d in response to an operation of the movable handle 36b1, which is an operating handle.

Configurations of a power supply unit 12, a liquid feeding unit 13 and a suction unit 14 are similar to those illustrated in FIG. 2. The content of processing performed by a CPU 41 is different from that in the first embodiment.

Figure 8:
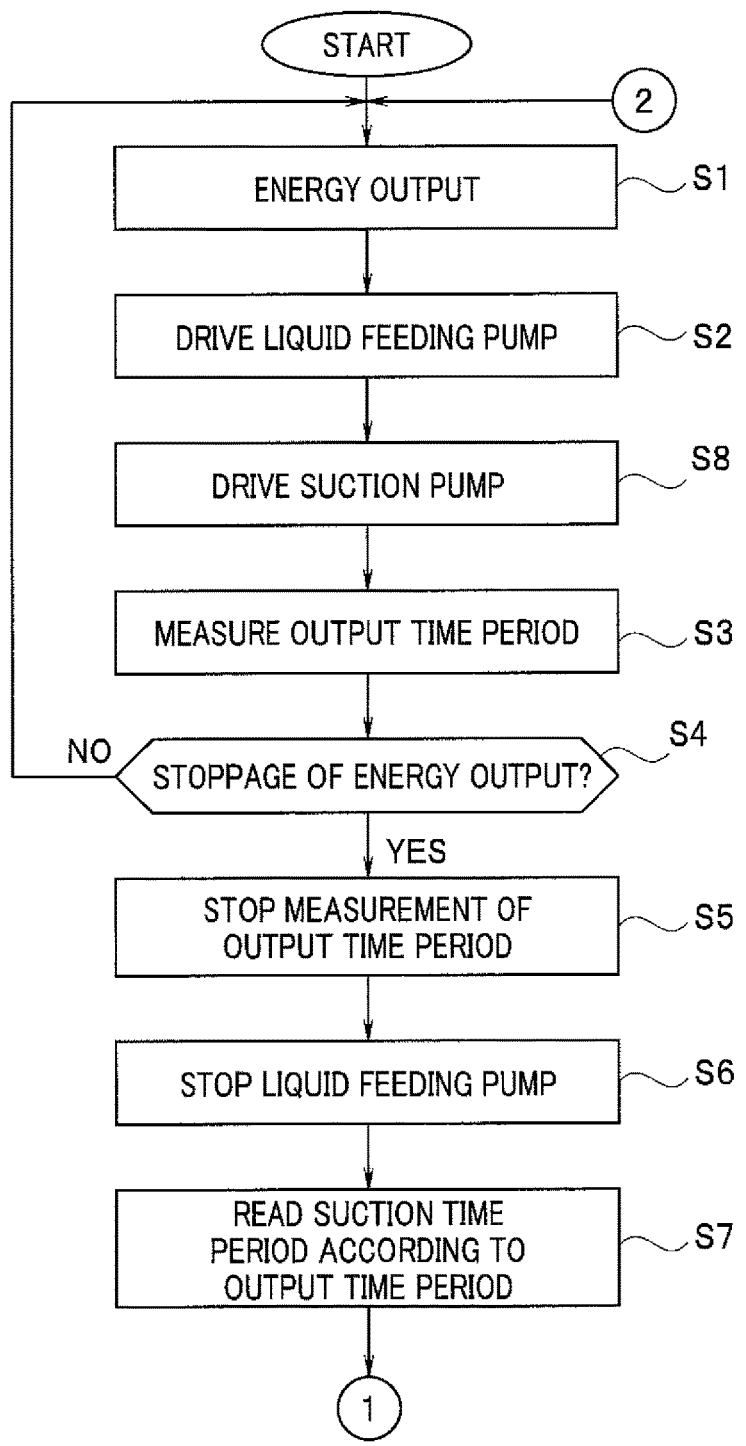
FIG. 8 is a flowchart illustrating an example of processing performed by a CPU 41 that controls an HF output section 44 and pump drive sections 46 and 48 according to the second embodiment of the present invention.
Figure 9:
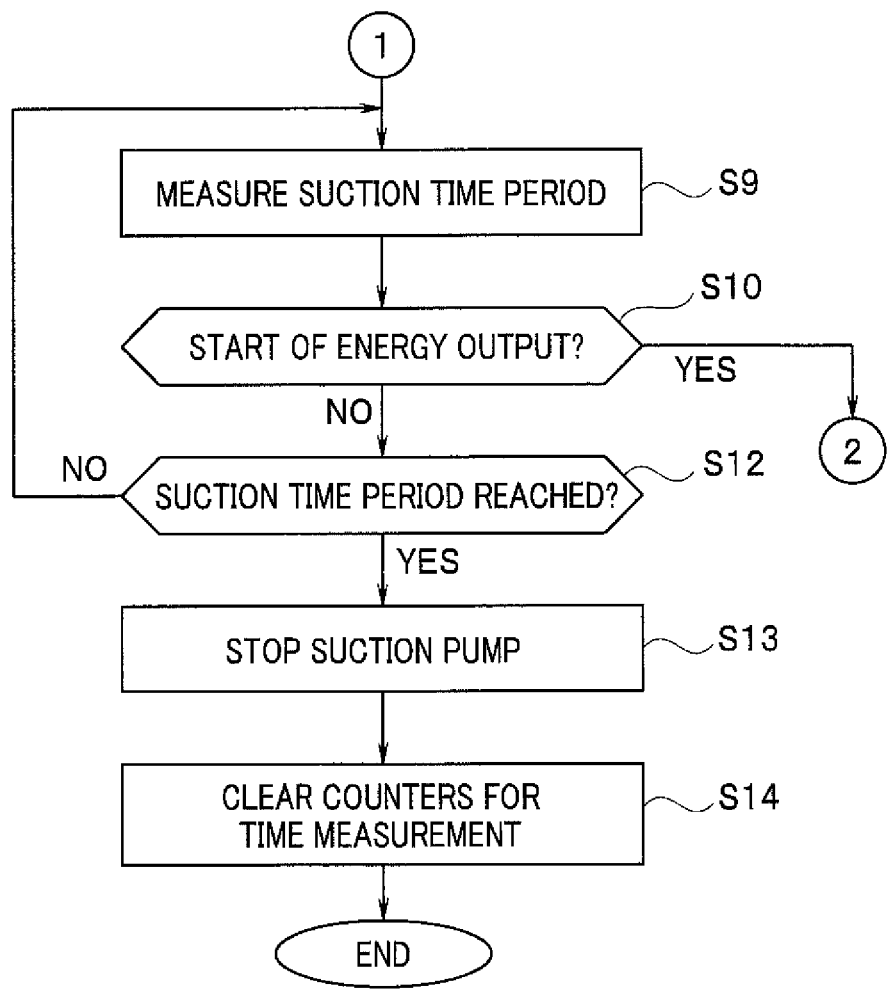
FIG. 9 is a flowchart illustrating an example of processing performed by the CPU 41 that controls the HF output section 44 and the pump drive sections 46 and 48 according to the second embodiment of the present invention.
Figure 10:
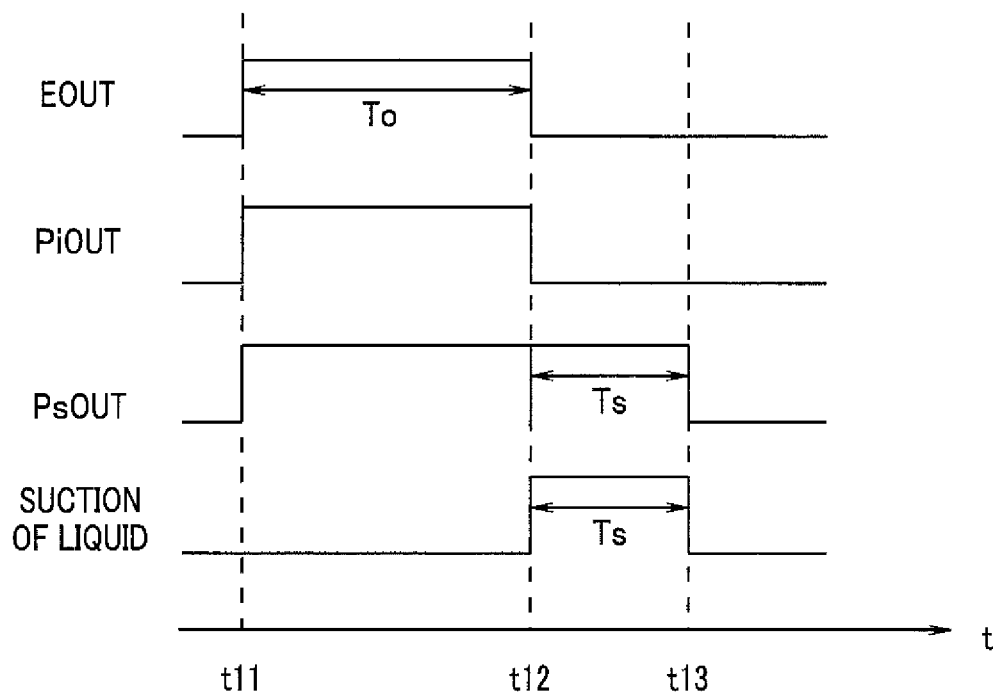
FIG. 10 is a timing chart of an output signal EOUT for a high-frequency current output, a pump drive signal PiOUT for a pump 47, a pump drive signal PsOUT for a pump 49, and saline suction from an opening portion 21c, according to the second embodiment of the present invention.

FIGS. 8 and 9 are flowcharts illustrating an example of processing performed by the CPU 41 that controls an HF output section 44 and pump drive sections 46 and 48. In FIGS. 8 and 9, processing steps that are the same as those in FIGS. 4 and 5 are provided with reference numerals that are the same as those in FIGS. 4 and 5, and only a simplified description thereof will be provided. FIGS. 8 and 9 are different from FIGS. 4 and 5 in terms of, e.g., the order of processing steps. FIG. 10 is a timing chart of an output signal EOUT for a high-frequency current output, a pump drive signal PiOUT for a pump 47, a pump drive signal PsOUT for the pump 49, and suction of saline from an opening portion 21c.

In FIG. 8, upon receipt of an instruction for an energy output provided by depression of a relevant one of switches 37, the CPU 41 provides an energy output designated by the instruction (S1), and subsequently, outputs a drive signal to the pump drive section 46 to drive the pump 47 to feed a liquid (S2). Then, the CPU 41 outputs a pump drive signal PsOUT to the pump drive section 48 to drive the pump 49 to perform suction (S8).

When the instruction for an energy output is provided, the handle portion 36A is closed, and thus, the projection portion 51 deforms the liquid feeding tube 21d. Accordingly, even if the pump 49 is driven, suction by the pump 49 is not performed. In FIG. 10, an output of an output signal EOUT is started at a time t11, but suction of saline is not performed.

Subsequent to S8, the CPU 41 starts measurement of an output time period (S3), and subsequently, determines whether or not the energy output is stopped (S4).

If no instruction for stopping the energy output is provided (S4: NO), the processing returns to S1. If an instruction for stopping the energy output is provided as a result of the depression of the switch 37 being discontinued (S4: YES), the CPU 41 stops the measurement of the output time period (S5), stops the liquid feeding pump 47 (S6), and reads a suction time period Ts according the measured output time period, which is stored in a storage section 42 (S7).

When the surgeon opens the handle portion 36A along with the stoppage of the energy output, the projection portion 51 no longer presses the suction tube 21d, and thus suction is started. As a result, saline is suctioned from the opening portion 21c at a distal end portion of a sheath portion 32 in the treatment instrument 11A. In FIG. 10, at a time t12, the energy output is stopped and suction is started.

After the stoppage of the energy output, the CPU 41 starts measurement of a suction time period (S9). The CPU 41 determines whether or not an instruction for a start of an energy output is provided by the switch 37 being operated when suction is performed (S10), and if an energy output is started (S10: YES), the handle portion 36A is closed, and the processing returns to S1. This is because an instruction according to a surgeon's operation is prioritized as in the first embodiment.

If no energy output is started (S10: NO), whether or not a period of time from the stoppage of the energy output has reached the read suction time period Ts is determined (S12), and if the period of time passed from the start of the suction has not reached the suction time period Ts yet (S12: NO), the processing returns to S9 and the suction is continued.

If the period of time from the start of the suction has reached the suction time period Ts (S12: YES), the CPU 41 discontinues the output of the pump drive signal PsOUT to the pump drive section 48 to stop the suction (S13) and thereby terminates the processing. In FIG. 10, at a time t13, the suction is stopped.

Accordingly, with the present embodiment, also, suction is performed for a set liquid feeding time period Ts, and thus, saline accumulated inside a body as a result of treatment for oozing bleeding is suctioned after an energy output.

As described above, with the above-described surgical apparatus 1A according to the present embodiment, when, e.g., treatment for oozing bleeding is provided, saline accumulated inside the body is suctioned, and thus, the accumulated saline is removed without the need for an assistant and without hindrance of the vision by a suction tube operated by an assistant, enabling a surgeon to promptly continue the surgical operation.

Note that although in the above-described example, an operation of the switch 37 for an energy output and an opening/closing operation of the handle portion 36A are independent from each other, a switch may be provided in the handle portion 36A so that when the switch is closed by an operation of the movable handle 36b1 in the handle portion 36A, the switch is turned on to generate an instruction signal for an energy output. For example, in FIG. 7, a projection portion 53, which is separate from the projection portion 51, is provided in the movable handle 36b1 indicated in parentheses, and a switch 54 that is pressed by the projection portion 53 when the handle portion 36A is closed is provided in the fixed handle 36a.

Such configuration enables an operation of a switch for an energy output and an opening/closing operation of the handle portion 36A can be linked to each other.

As described above, with the surgical apparatus according to each of the above-described embodiments, when, e.g., treatment for oozing bleeding is provided, saline accumulated inside the body is promptly removed, enabling a surgeon to promptly continue the surgical operation.

The surgical apparatus according to each of the above-described embodiments is effective especially for energy-used treatment for the parenchyma of a liver. In the case of the parenchyma of a liver, which is surrounded by a membrane, oozing bleeding easily occurs. In such cases, with the surgical apparatus according to each of the above-described embodiments, saline is promptly removed after an end of an energy output for treatment, enabling a surgeon to promptly continue the surgical operation.

Note that the surgical apparatus according to each of the embodiments is effectively applicable not only to the parenchyma of a liver, but also to, e.g., other organs such as blood vessels.

(Modification 1)

Although in each of the two embodiments described above, suction is performed for a predetermined period of time after an end of an energy output, it is possible that suction is performed in a predetermined amount instead of the suction being performed for a predetermined period of time. In other words, a CPU 41 may control a pump 49 so as to suction a predetermined amount of liquid according to an output time period or a liquid feeding time period at the time of an output for energy-used treatment.

In such case, also, information on the predetermined amount, that is, a suction amount, is stored in a storage section 42, and as in the two embodiments described above, the predetermined amount is set so as to vary according to a measured output time period or a measured liquid feeding period. Furthermore, values of the liquid feeding amounts stored in the storage section 42 can be set/changed by a surgeon.

(Modification 2)

Although in the two embodiments and modification 1 described above, a suction time period or a suction amount is a suction time period or a suction amount set in advance in the storage section 42 according to an energy output time period or a liquid feeding time period, a suction pattern such as a suction time period may be changed according to a value of an impedance of a living tissue pinched between a probe 31a and a movable member 31b, which is detected by an impedance detection section 45.

(Modification 3)

Although in the two embodiments and modification 1 described above, a suction time period or a suction amount is a suction time period or a suction amount set in advance in a storage section 42 according to an energy output time period or a liquid feeding time period, a surgeon may set a suction time period or a suction amount via an operating panel 40 to perform suction for the set suction time period or in the set suction amount irrespective of the energy output time period or the liquid feeding time period.

Accordingly, a CPU 41 controls a pump 49 so as to perform suction for the set suction time period or in the set suction amount after an end of an energy output.

(Modification 4)

Although in the two embodiments and the respective modifications described above, a liquid feeding tube 21*b* and a suction tube 21*d* are each provided inside a treatment instrument 11 or 11A, provision of the tubes inside a sheath portion 32 causes the problem of an increase in diameter of the sheath portion 32. Therefore, at least one of the liquid feeding tube 21*b* and the suction tube 21*d* may be substituted by a space between an inner pipe and an outer pipe inside the sheath portion 32 or a space between the inner pipe and a probe 31*a*.

In such case, the inside and the outside of each of the inner pipe and the outer pipe are coated with an insulating material. This is intended to prevent occurrence of electrical conduction even if saline exists between the inner pipe and the outer pipe or between the inner pipe and the probe 31*a*.

For example, where saline is made to flow on the outside of the probe 31*a*, an electrical short between the circuit probe 31*a* and the inner pipe can be prevented. Furthermore, where saline is made to flow between the inner pipe and the outer pipe, an electrical short between the inner pipe and the outer pipe can be prevented.

Coating of the insides of the inner pipe and the outer pipe with an insulating material can be performed by inserting an injection nozzle to the inside of each of the pipes and injecting the insulating material from the nozzle while the nozzle is moved inside the pipe.

Such configuration enables supply of saline to a treatment section 31 without an increase in diameter of the sheath portion 32. Furthermore, provision of insulating coating as described above reduces resistance to slide relative to the outer pipe if the inner pipe is a drive shaft for the scissors shape type.

The present invention is not limited to the above-described embodiments, and various modifications, alterations and the like are possible without departing from the spirit of the present invention.

What is claimed is:

1. A surgical apparatus comprising:
   a treatment section for treating a living tissue;
   an energy generation section for providing high-frequency current to the treatment section;
   a liquid feeding conduit for feeding a liquid to the living tissue;
   a suction conduit for suctioning the liquid;
   an energy control section configured to output a high-frequency output control signal for controlling the high-frequency current from the energy generation section;
   a first pump drive section configured for feeding the liquid from the liquid feeding conduit while the high-frequency current is output in response to a command for an output of the high-frequency output control signal from the energy control section, and configured to stop the feeding of the liquid from the liquid feeding, conduit when the first pump drive section receives a command for stopping the high-frequency output control signal, wherein the first pump drive section causes the feeding of the liquid from the liquid feeding conduit to terminate simultaneously with stopping the high-frequency output control signal;
   a second pump drive section configured to cause the suction conduit to suction the liquid for a predetermined period of time or in a predetermined amount, only after the second pump drive section receives the command for stopping the high-frequency output control signal from the energy control section, and configured to stop the suction of the liquid from the suction conduit after suctioning for the predetermined period of time or in the predetermined amount; and
   an impedance detection section configured to detect an impedance between two pinching members of the treatment section that are configured to pinch the living tissue,
   wherein the predetermined period of time or the predetermined amount is configured to vary according to the impedance detected by the impedance detection section.

2. The surgical apparatus according to claim 1, wherein the predetermined period of time or the predetermined amount is stored in a storage section and can be set or changed.

3. The surgical apparatus according to claim 1, wherein the predetermined period of time or the predetermined amount is set according to a period of time of outputting the high-frequency current or a period of time of driving the first pump drive section.

4. The surgical apparatus according to claim 1, wherein upon receipt of an instruction for generating the high-frequency current to the energy generation section after stopping the high-frequency output control signal, the energy control section is configured to stop the second pump drive section suctioning the liquid from the liquid feeding conduit.

5. The surgical apparatus according to claim 1, further comprising
   a pump configured to connect with the suction conduit, wherein the energy control section is configured to perform control so that driving of the pump is started so as to perform the suction of the liquid via the pump in response to after stopping the high-frequency output control signal, and the pump is stopped after suctioning the liquid via the pump for the predetermined period of time or in the predetermined amount.

* * * * *